US010874351B2

(12) United States Patent
Chen

(10) Patent No.: US 10,874,351 B2
(45) Date of Patent: Dec. 29, 2020

(54) PHYSIOLOGICAL SIGNAL DETECTING APPARATUS AND PHYSIOLOGICAL SIGNAL DETECTING DEVICE

(71) Applicant: ZENTAN TECHNOLOGY CO., LTD., New Taipei (TW)

(72) Inventor: Tong-Pie Chen, New Taipei (TW)

(73) Assignee: ZENTAN TECHNOLOGY CO., LTD., New Taipei (TW)

( * ) Notice: Subject to any disclaimer, the term of this patent is extended or adjusted under 35 U.S.C. 154(b) by 345 days.

(21) Appl. No.: 15/870,754

(22) Filed: Jan. 12, 2018

(65) Prior Publication Data

US 2018/0132791 A1 May 17, 2018

Related U.S. Application Data

(63) Continuation-in-part of application No. 14/722,024, filed on May 26, 2015, now Pat. No. 9,986,792.

(30) Foreign Application Priority Data

Mar. 20, 2015 (TW) .............................. 104204208 U

(51) Int. Cl.
| | |
|---|---|
| *A61B 5/00* | (2006.01) |
| *A61B 5/0408* | (2006.01) |
| *A61B 5/0416* | (2006.01) |
| *A61B 5/024* | (2006.01) |

(52) U.S. Cl.
CPC .......... *A61B 5/7203* (2013.01); *A61B 5/0002* (2013.01); *A61B 5/0416* (2013.01); *A61B 5/04085* (2013.01); *A61B 5/6802* (2013.01); *A61B 5/6831* (2013.01);
(Continued)

(58) Field of Classification Search
CPC ................ A61B 5/6831; A61B 5/6868; A61B 2562/225; A61B 5/7203; A61B 5/0002; A61B 5/04085; A61B 5/0416; A61B 5/6802; A61B 5/02438; A61B 5/0408;
(Continued)

(56) References Cited

U.S. PATENT DOCUMENTS

| | | | | |
|---|---|---|---|---|
| 9,504,294 B2 * | 11/2016 | Hasegawa | .......... | A44B 17/0052 |
| 2002/0029444 A1 * | 3/2002 | Lyle | ................... | A44B 17/0029 |
| | | | | 24/621 |

(Continued)

*Primary Examiner* — Tammie K Marlen
(74) *Attorney, Agent, or Firm* — Li & Cai Intellectual Property (USA) Office

(57) ABSTRACT

A physiological signal detecting device includes a carrier, an electrode layer fixed on the carrier for receiving a physiological signal, and a signal transmitter buckled on the electrode layer and the carrier. The signal transmitter includes a transmitting member and an external connector. The transmitting member includes a first sheet, a column extending from the first sheet, and a thorn curvedly extending from the first sheet. The external connector includes a ring-shaped second sheet and a hollow protrusion extending from an inner edge of the second sheet. The thorn has a sharp end piercing into the electrode layer, the column passes through the electrode layer and the carrier, and a free end portion of the column exposes from the carrier. The protrusion is sleeved at and fastened to the free end portion so that the carrier and the electrode layer are sandwiched between the first and second sheets.

10 Claims, 6 Drawing Sheets

(52) U.S. Cl.
CPC ......... *A61B 5/02438* (2013.01); *A61B 5/0408* (2013.01); *A61B 2562/18* (2013.01); *A61B 2562/225* (2013.01)

(58) Field of Classification Search
CPC ............ A61B 2562/18; A44B 17/0023; A44B 17/0041; A44B 17/007; A44B 17/0076
See application file for complete search history.

(56) References Cited

U.S. PATENT DOCUMENTS

| | | | |
|---|---|---|---|
| 2015/0157265 A1* | 6/2015 | Kang ................... | A61B 5/6831 600/394 |
| 2015/0223716 A1* | 8/2015 | Korkala ............... | A61B 5/0245 600/393 |

* cited by examiner

PHYSIOLOGICAL SIGNAL DETECTING APPARATUS AND PHYSIOLOGICAL SIGNAL DETECTING DEVICE

CROSS REFERENCE TO RELATED APPLICATION

This application is a continuation-in-part of U.S. patent application Ser. No. 14/722,024 filed on May 26, 2015 and entitled "SNAP BUTTON AND PHYSIOLOGICAL SIGNAL DETECTING BELT THEREOF FOR IMPROVING ELECTRIC CONDUCTIVITY", now issued as U.S. Pat. No. 9,986,792.

BACKGROUND OF THE INVENTION

1. Field of the Invention

The present disclosure relates to a detecting apparatus; in particular, to a physiological signal detecting apparatus and a physiological signal detecting device.

2. Description of Related Art

A snap button on the market is generally used to dispose the fabric between its male and female retaining members, and the male and female retaining members are united by mechanical stamping or other methods so that the fabric can be compressed between the male and female retaining members. However, the fabric is still loose and cannot be held tightly by the male and female retaining members.

As technology advances, conventional medical devices used in measuring various human physiological signals have been designed smaller and wireless so as to let people or patients measure their own physiological signals anytime and anywhere, not only for diseases that may be effectively controlled but also to decrease the frequency of seeing the doctor or accident events. Furthermore, this can be used for determining athletes' physiological status when they are training.

There are some physiological sensing belts on the market, that are surroundingly bundled on a human's chest to detect the physiological signals via a conductive fiber on the inner surface of the belt making contact with human's skin, and the physiological signals would be read, analyzed, and displayed by the snap button disposed on the conductive fiber and a signal transceiver fastened to each other to wirelessly transmit the signals to an external electronic device.

However, the detected physiological signals are highly connected with the electrical connectivity among the snap button, conductive fiber, and signal transceiver. If there is poor electrical contact between the snap button and the conductive fiber, it is liable to receive inaccurate and noisy physiological signals. Meanwhile, a contacted surface between the snap button and the conductive fiber is easily oxidized by sweat, causing problems such as inaccuracy and lots of noise in the signals.

SUMMARY OF THE INVENTION

The present disclosure provides a physiological signal detecting apparatus and a physiological signal detecting device to solve the drawbacks associated with conventional physiological signal detecting devices.

The present disclosure discloses a physiological signal detecting apparatus, which includes a physiological signal detecting device and a signal transceiver. The physiological signal detecting device includes a carrier, two electrode layers, and two signal transmitters. The carrier has a first surface and a second surface opposite the first surface. The two electrode layers are separately fixed on the first surface of the carrier. The two signal transmitters are separately buckled on the two electrode layers and the carrier. The two signal transmitters respectively contact the two electrode layers, and each of the two signal transmitters consists of a transmitting member and an external connector. The transmitting member is integrally formed as one-piece structure and includes a first sheet, a column perpendicularly extending from the first sheet, and a plurality of thorns curvedly extending from the first sheet. The first sheet abuts against the corresponding electrode layer, each of the thorns has a sharp end piercing into the corresponding electrode layer, the column passes through the corresponding electrode layer and the carrier, and a free end portion of the column exposes from the carrier. The external connector is integrally formed as one-piece structure and includes a ring-shaped second sheet and a hollow protrusion extending from an inner edge of the second sheet. The protrusion is sleeved at and fastened to the free end portion of the column so that the carrier and the corresponding electrode layer are sandwiched between the second sheet and the first sheet. The signal transceiver includes two electrical contacts respectively and detachably positioned at the protrusions of the two signal transmitters. Each of the two electrode layers is configured for receiving a physiological signal, and each of the two signal transmitters is configured for transmitting the physiological signal from the corresponding electrode layer to the signal transceiver through the thorns thereof.

The present disclosure also discloses a physiological signal detecting device, which includes a carrier, an electrode layer, and a signal transmitter. The carrier has a first surface and a second surface opposite the first surface. The electrode layer is fixed on the first surface of the carrier. The signal transmitter is buckled on the electrode layer and the carrier and includes a transmitting member and an external connector. The transmitting member is integrally formed as one-piece structure and includes a first sheet, a column perpendicularly extending from the first sheet, and a thorn curvedly extending from the first sheet. The first sheet abuts against the electrode layer, the thorn has a sharp end piercing into the electrode layer, the column passes through the electrode layer and the carrier, and a free end portion of the column exposes from the carrier. The external connector is integrally formed as one-piece structure and includes a ring-shaped second sheet and a hollow protrusion extending from an inner edge of the second sheet. The protrusion is sleeved at and fastened to the free end portion of the column so that the carrier and the electrode layer are sandwiched between the second sheet and the first sheet. The electrode layer is configured for receiving a physiological signal, and the signal transmitter is configured for transmitting the physiological signal from the electrode layer through the thorn.

In summary, for the physiological signal detecting apparatus and the physiological signal detecting device of the present disclosure, the signal transmitter adapts the thorn thereof to pierce into the electrode layer so that the carrier and the electrode layer can be sandwiched between the first sheet and the second sheet of the signal transmitter. Thus, the structural and electrical connection between the transmitting member and the electrode layer can be improved so as to accurately transmit the physiological signal to the signal transceiver.

Moreover, the thorn of the transmitting member of the present disclosure can be prevented from oxidation and can prevent the transmitting member from rotating relative to the electrode layer by piercing into the electrode layer, thereby avoiding receiving inaccurate and noisy physiological signals.

In order to further appreciate the characteristics and technical contents of the present disclosure, references are hereunder made to the detailed descriptions and appended drawings in connection with the present disclosure. However, the appended drawings are merely shown for exemplary purposes, and should not be construed as restricting the scope of the present disclosure.

DETAILED DESCRIPTION OF THE PREFERRED EMBODIMENTS

Reference is made to FIGS. 1 to 6, which illustrate an embodiment of the present disclosure. References are hereunder made to the detailed descriptions and appended drawings in connection with the present disclosure. However, the appended drawings are merely provided for exemplary purposes, and should not be construed as restricting the scope of the present disclosure.

Figure 1:
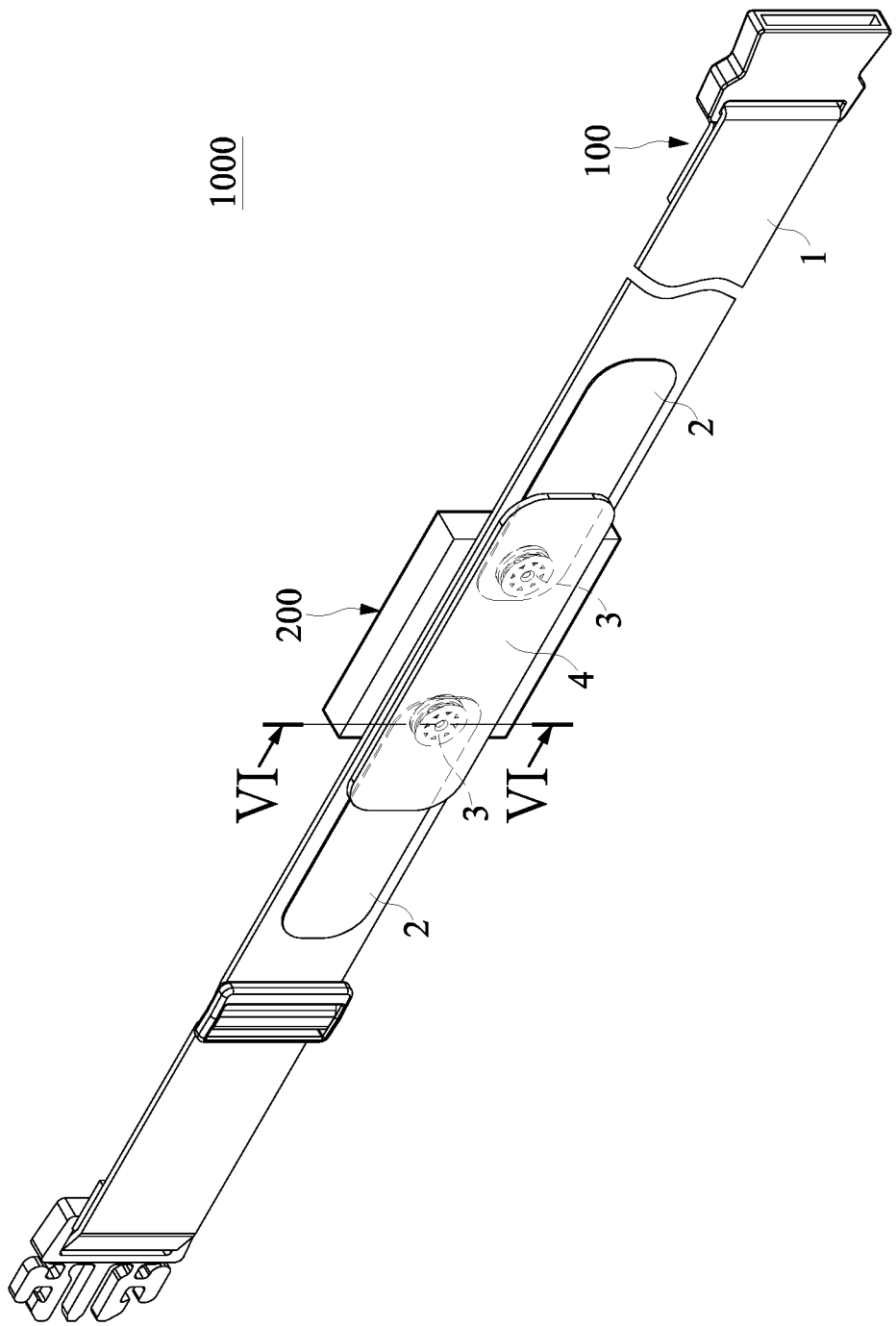
FIG. 1 is a perspective view showing a physiological signal detecting apparatus according to the present disclosure.
Figure 2:
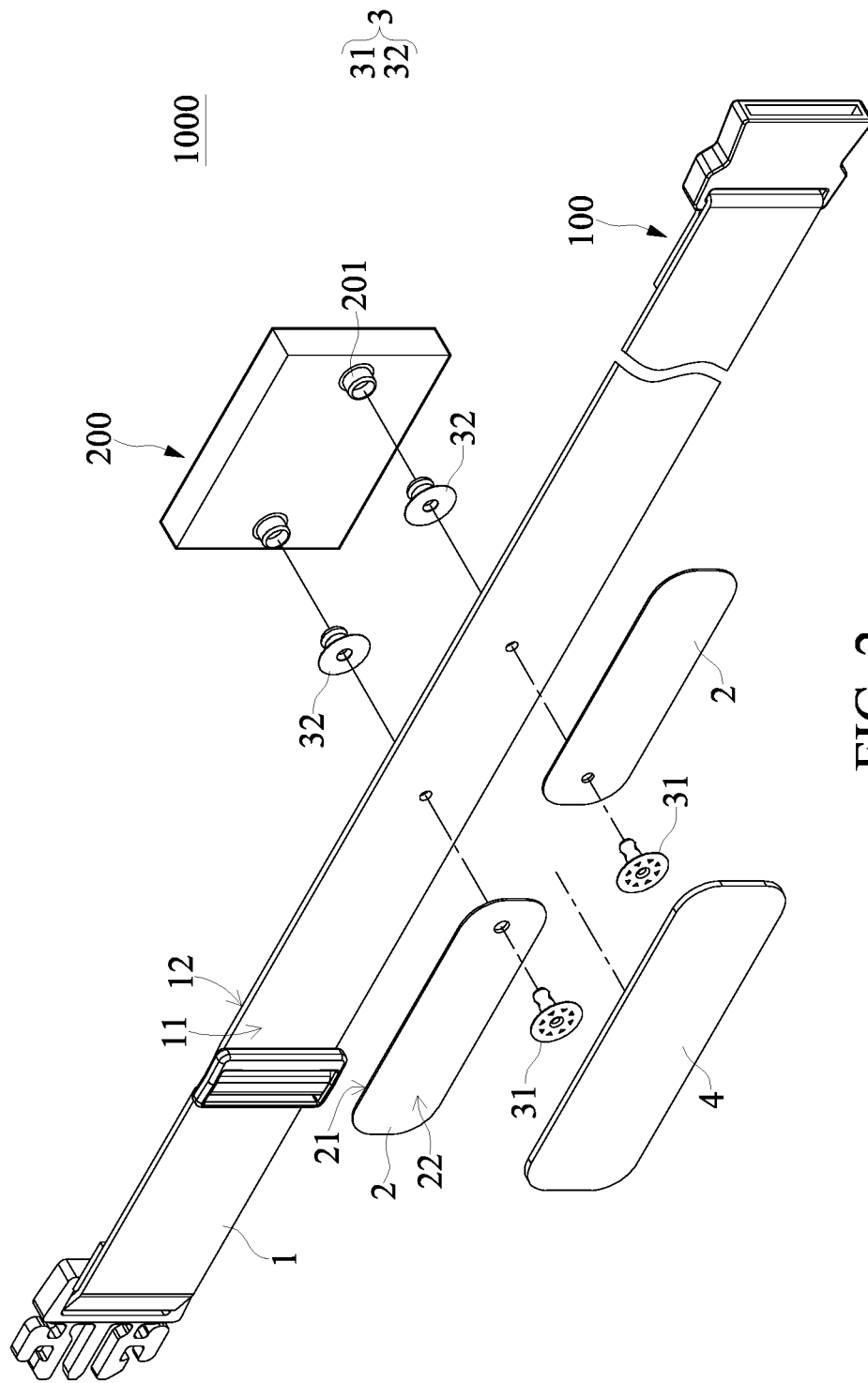
FIG. 2 is an exploded view of FIG. 1.
Figure 3:
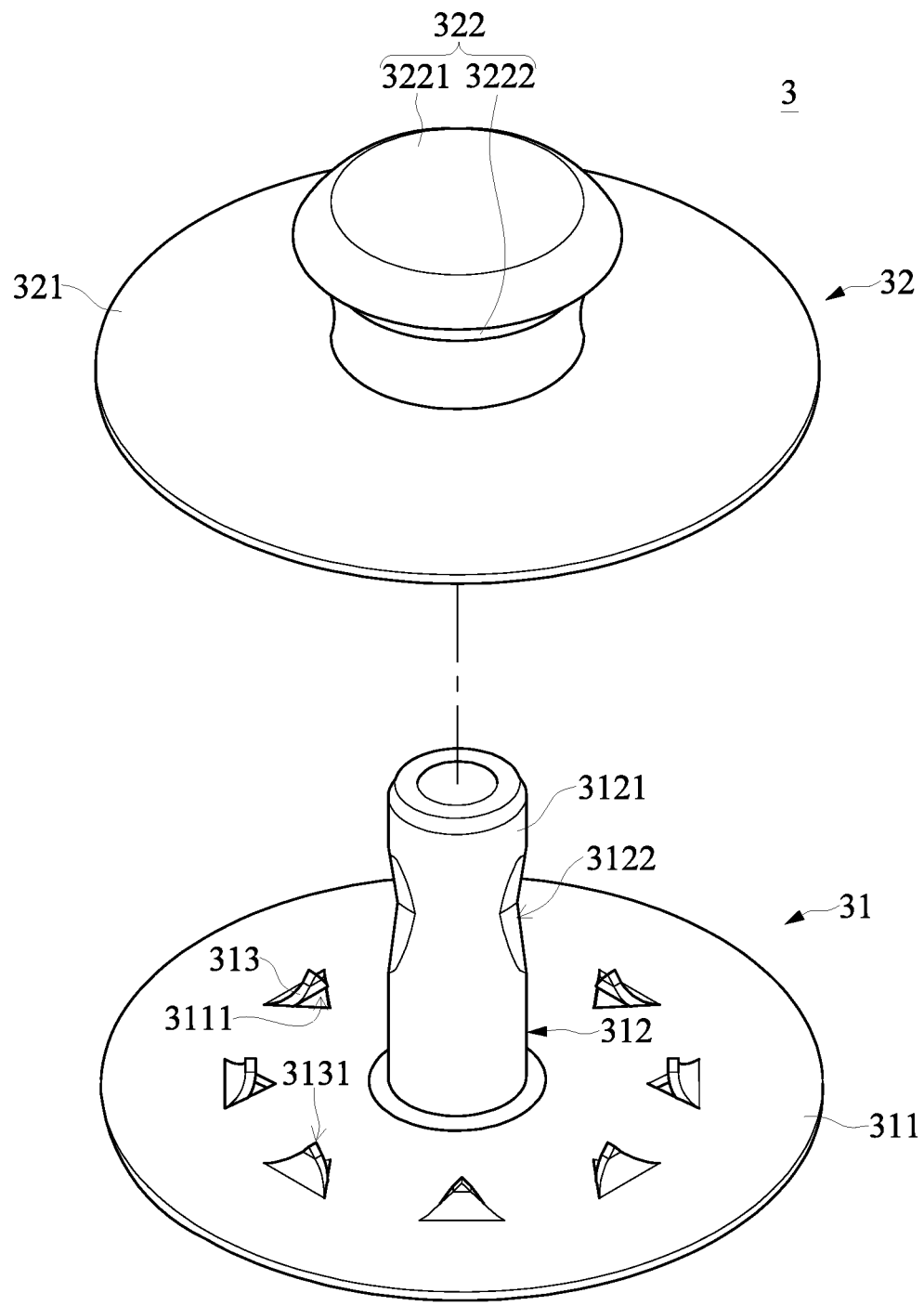
FIG. 3 is an exploded view showing a signal transmitter of the physiological signal detecting apparatus according to the present disclosure.
Figure 4:
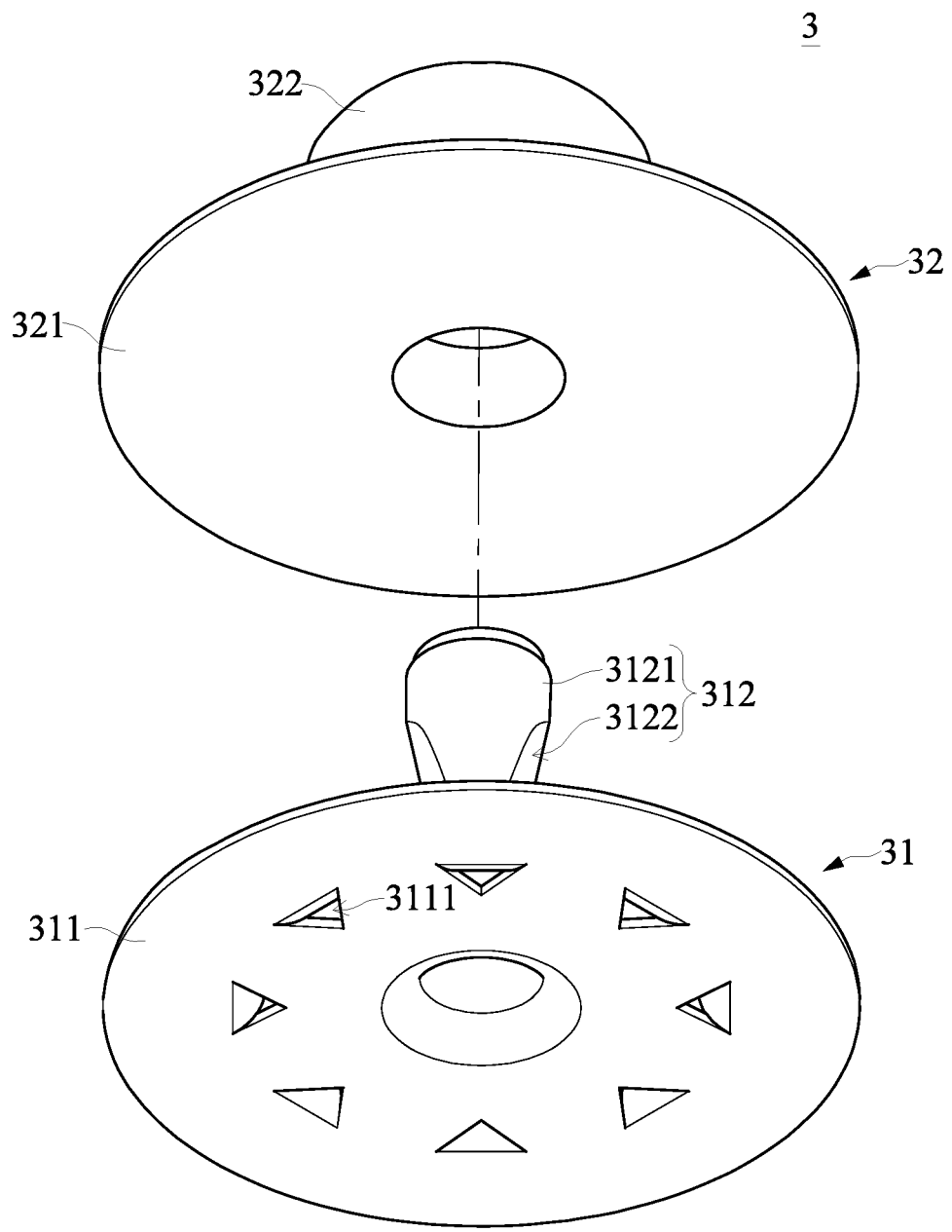
FIG. 4 is an exploded view showing the signal transmitter of the physiological signal detecting apparatus in another perspective according to the present disclosure.
Figure 5:
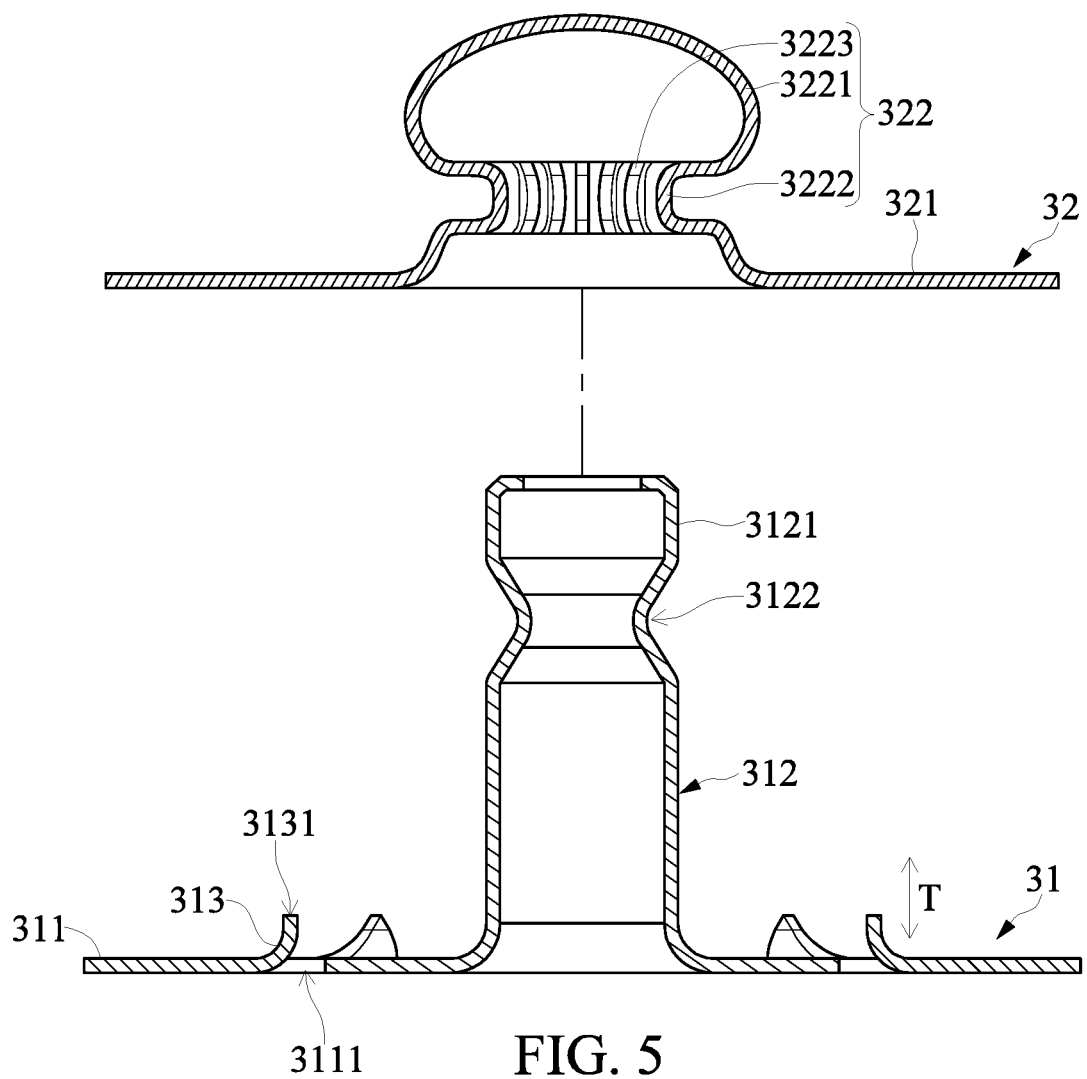
FIG. 5 is a planar cross-sectional view of FIG. 3.
Figure 6:
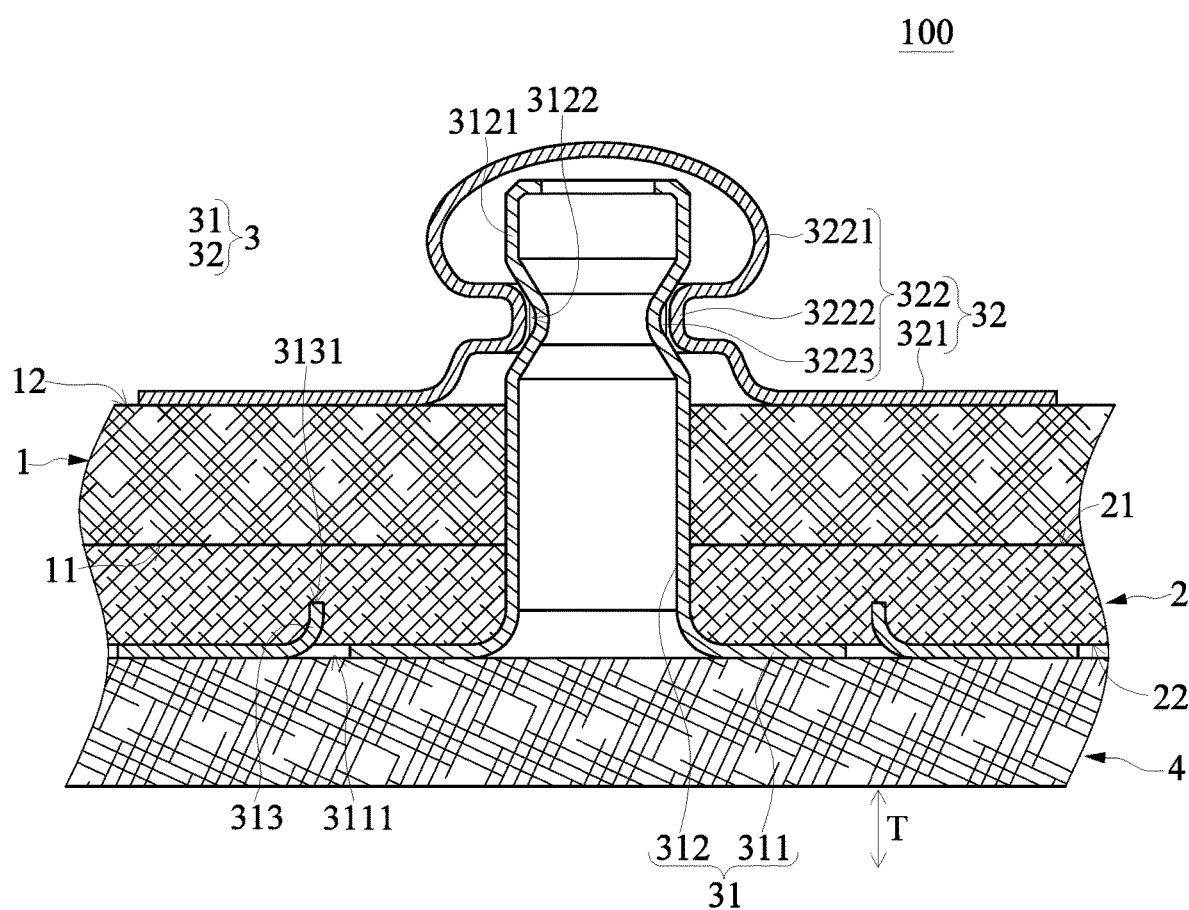
FIG. 6 is a cross-sectional view taken along a cross-sectional line VI-VI of FIG. 1 in which the signal transceiver is omitted.

As shown in FIGS. 1 and 2, the present embodiment discloses a physiological signal detecting apparatus 1000 for contacting an object (e.g., a person) and receiving a physiological signal from the object. The physiological signal detecting apparatus 1000 includes a physiological signal detecting device 100 and a signal transceiver 200 cooperated with the physiological signal detecting device 100. It should be noted that the physiological signal detecting device 100 and the signal transceiver 200 in the present embodiment are cooperated with each other, but the present disclosure is not limited thereto. The following description discloses the structure and connection relationship of each component of the physiological signal detecting device 100, and then discloses the connection relationship between the physiological signal detecting device 100 and the signal transceiver 200.

The physiological signal detecting device 100 includes a carrier 1, two electrode layers 2 separately fixed on the carrier 1, two signal transmitters 3 separately buckled on the two electrode layers 2 and the carrier 1, and an isolator 4 disposed on the two electrode layers 2 and covering the two signal transmitters 3. It should be noted that the number of the electrode layers 2 or the signal transmitters 3 in the present embodiment is two, but the present disclosure is not limited thereto. For example, in other embodiments of the present disclosure, the number of the electrode layers 2 or the signal transmitters 3 can be at least one.

The carrier 1 in the present embodiment can be fabricated from, but is not limited to natural fibers, artificial fibers, and combinations thereof. Examples of the natural fibers include, but are not limited to cotton, hemp, silk, and wool. Examples of the artificial fibers include, but are not limited to rayon fibers, nylon fibers, polyester fibers or acrylic fibers. The fabric can be any knitting patterns, e.g., flat-woven, non-woven, mesh-woven, or knitted fabric. Moreover, the carrier 1 has a first surface 11 and a second surface 12 opposite the first surface 11, and the carrier 1 in the present embodiment is an elongated belt, but the present disclosure is not limited thereto. For example, in other embodiments of the present disclosure, the carrier 1 can be a cloth, a pair of pants, a sock, a towel, or other objects, which may contact a person's skin.

The two electrode layers 2 are separately fixed on the first surface 11 of the carrier 1. Each of the two electrode layers 2 in the present embodiment can be a cloth or colloid having electric conductivity such as a conductive fiber, conductive fabric, conductive rubber, or multilayer composite material. Each of the two electrode layers 2 can be bound to the first surface 11 of the carrier 1 by using the molding methods such as hot pressing, coating, spinning and weaving, textile printing, or sewing, but the present disclosure is not limited thereto. Moreover, each of the two electrode layers 2 includes a fixing surface 21 and a contacting surface 22 opposite the fixing surface 21, and the fixing surface 21 is disposed on the first surface 11.

The two signal transmitters 3 respectively contact the two electrode layers 2. Each of the two signal transmitters 3 is manufactured by a conductive material, and includes a transmitting member 31 and an external connector 32 detachably connected to the transmitting member 31. In the present embodiment, each of the two signal transmitters 3 can consist of the transmitting member 31 and the external connector 32. That is to say, the signal transmitter 3 of the present embodiment is only formed by assembling two pieces, but the present disclosure is not limited thereto.

As the two signal transmitters 3 are of the same structure, the following description discloses the structure of just one of the two signal transmitters 3 and the corresponding electrode layer 2 for the sake of brevity. However, in other embodiments of the present disclosure, the two signal transmitters 3 can be of the different structure.

As shown in FIGS. 3 to 6, the transmitting member 31 is integrally formed as one-piece structure, and the transmitting member 31 in the present embodiment is manufactured by punching or drawing a single metal sheet, but the present disclosure is not limited thereto. The transmitting member 31 includes a first sheet 311, a column 312 perpendicularly extending from the first sheet 311, and a plurality of thorns 313 curvedly extending from the first sheet 311.

In the present embodiment, the first sheet 311 has a ring-shape, and the column 312 is a tubular structure perpendicularly extending from an inner edge of the first sheet 311. The first sheet 311 has a plurality of notches 3111 in a ring-shaped arrangement, and each of the notches 3111 has an acute angle aligning a center of the first sheet 311. Moreover, the thorns 313 respectively correspond in shape to the notches 3111. In other words, each of the thorns 313 has a sharp end 3131 having an acute angle, the volume of each of the thorns 313 is equal to that of the corresponding notch 3111, and each of the thorns 313 curvedly extends from an inner wall of the corresponding notch 3111 (i.e., the opposite side corresponding to the acute angle of the notch 3111).

Specifically, the first sheet 311 abuts against the contacting surface 22 of the corresponding electrode layer 2. The sharp end 3131 of each of the thorns 313 pierces into the corresponding electrode layer 2 through the contacting surface 22, and each of the thorns 313 is entirely embedded in the corresponding electrode layer 2. The column 312 passes through the corresponding electrode layer 2 and the carrier 1.

A free end portion 3121 of the column 312 exposes from the carrier 1, and the free end portion 3121 of the column 312 has a buckling trough 3122. The buckling trough 3122 in the present embodiment includes two parts, and a distance between the two parts of the buckling trough 3122 first decreases and then increases in a direction away from the first sheet 311.

Moreover, each of the thorns 313 includes an outer surface having an arced shape and defining a tangential direction T parallel to the sharp end 3131 thereof, and the tangential direction T defined by each of the thorns 313 is substantially perpendicular to the corresponding electrode layer 2. For example, an angle between the tangential direction T and the corresponding electrode layer 2 can be within a range of 80~100 degrees. A cross-section of each of the thorns 313 perpendicular to the tangential direction T has an area, which gradually decreases in a direction away from the first sheet 311. For example, each of the thorns 313 is similar to a triangular shape.

In other embodiments of the present disclosure, the first sheet 311 can be formed without the notches 3111, and the thorns 313 extend from an outer edge of the first sheet 311. For the transmitting member 31, the number of the thorns 313 can be at least one.

The external connector 32 is integrally formed as one-piece structure, and the external connector 32 in the present embodiment is manufactured by punching or drawing a single metal sheet, but the present disclosure is not limited thereto. The external connector 32 includes a ring-shaped second sheet 321 and a hollow protrusion 322 extending from an inner edge of the second sheet 321. Specifically, space inside the protrusion 322 is in communication with an outer space just through a center hole of the second sheet 321.

The protrusion 322 is sleeved at and fastened to the free end portion 3121 of the column 312 so that the carrier 1 and the corresponding electrode layer 2 are sandwiched between the second sheet 321 and the first sheet 311. The first sheet 311 and the second sheet 321 of the signal transmitter 3 can respectively and flatly abut against the contacting surface 22 of the corresponding electrode layer 2 and the second surface 12 of the carrier 1 by using the thorns 313 to pierce into and to be embedded in the corresponding electrode layer 2.

Moreover, the electrical connection between the transmitting member 31 and the external connector 32 can be maintained by using the protrusion 322 to buckle the free end portion 3121 of the column 312. The electrical connection between the transmitting member 31 and the corresponding electrode layer 2 can be maintained by piercing and embedding the thorns 313 into the corresponding electrode layer 2, thereby preventing the electrical connection from instantaneously breaking due to movement of the person, in which the person wears the physiological signal detecting device 100.

Specifically, in the present embodiment, the second sheet 321 has a circular ring shape. The protrusion 322 includes a head portion 3221 and a neck portion 3222 connected to the head portion 3221 and the inner edge of the second sheet 321. The neck portion 3222 of the protrusion 322 is detachably buckled to the buckling trough 3122 of the column 312. A projecting region defined by orthogonally projecting the first sheet 311 in a longitudinal direction of the column 312 onto the second sheet 321 has an outer edge substantially overlapped at an outer edge of the second sheet 321, but the present disclosure is not limited thereto.

Furthermore, the neck portion 3222 includes a plurality of ribs 3223 formed by punching an outer surface thereof, and the ribs 3223 are in a ring-shaped arrangement. At least two of the ribs 3223 detachably buckle the buckling trough 3112, so the neck portion 3222 and the buckling trough 3112 are in a multi-point connection, thereby improving the stability of electrical connection between the transmitting member 31 and the external connector 32.

In addition, the structure of the head portion 3221 of the external connector 32 in the present embodiment can be changed or adjusted according to design requirements. For example, in other embodiments of the present disclosure, the head portion 3221 can be formed as a hollow hook, or the head portion 3221 can have a slot formed in a center of the top surface thereof.

The isolator 4 is disposed on and covers the first sheets 311 of the two signal transmitters 3, a part of each of the two electrode layer 2, and a part of the first surface 11 of the carrier 1 arranged around the first sheets 311. In other words, the first sheet 311 of each of the two signal transmitters 31 is covered by and sandwiched between the isolator 4 and the corresponding electrode layer 2, so the person does not directly contact the first sheet 311 of each of the two signal transmitters 31 for preventing the signal transmitting performance of the signal transmitters 3 from being affected by the person.

The isolator 4 in the present embodiment is manufactured by an insulating material, and the isolator 4 can be bound to the first surface 11 of the carrier 1 using the binding methods, e.g., gluing, sewing, ultrasonic bonding, or hot laminating, but the present disclosure is not limited thereto.

The structure and connection relationship of each component of the physiological signal detecting device 100 have been disclosed in the above description. Moreover, at least part of the contacting surface 22 of each of the two electrode layers 2 (i.e., a part of each contacting surface 22 is not covered by the isolator 4) is configured for receiving a physiological signal by contacting a person, and the corresponding transmitting member 31 is configured for transmitting the physiological signal from the at least part of the contacting surface 22 to the head portion 3221 of the external connector 32.

The signal transceiver 200 includes two electrical contacts 201 respectively and detachably positioned at the protrusions 322 of the two signal transmitters 3. The structure of the head portions 3221 of the protrusions 322 of the two external connectors 32 can be changed according to the structure of the two electrical contacts 201 of the signal transceiver 200, thereby each electrical contact 201 and the corresponding protrusion 322 can be formed in a desired cooperation (e.g., an inserting cooperation, a clamping cooperation, or an abutting cooperation).

Moreover, when a person wears the physiological signal detecting device 100, each of the two electrode layers 2 can receive a physiological signal from the person, and each of the two signal transmitters 3 can transmit the physiological signal from the corresponding electrode layer 2 to the signal transceiver 200 through the thorns 313 thereof.

[The Effects Associated with the Present Embodiments]

In summary, for the physiological signal detecting apparatus 1000 and the physiological signal detecting device 100 of the present disclosure, each of the two signal transmitters 3 adapts the thorns 313 thereof to pierce into the corresponding electrode layer 2 so that the carrier 1 and the corresponding electrode layer 2 can be sandwiched between the first sheet 311 and the second sheet 321. Thus, the structural and electrical connection between the transmitting member 31 and the corresponding electrode layer 2 can be improved so as to accurately transmit the physiological signal to the signal transceiver 200.

Moreover, the thorns 313 of the transmitting member 31 of the present disclosure can be prevented from oxidation and can prevent the transmitting member 31 from rotating relative to the electrode layer 2 by piercing into the electrode layer 2, thereby avoiding receiving inaccurate and noisy physiological signals.

In addition, the external connector 32 of the signal transmitter 3 is formed with the protrusion 322 extending from the second sheet 321, and the structure of the protrusion 322 can be changed according to the structure of the electrical contact 201 of the signal transceiver 200, thereby the electrical contact 201 and the protrusion 322 can be formed in a desired cooperation.

The descriptions illustrated supra set forth simply the preferred embodiments of the present disclosure; however, the characteristics of the present disclosure are by no means restricted thereto. All changes, alterations, or modifications conveniently considered by those skilled in the art are deemed to be encompassed within the scope of the present disclosure delineated by the following claims.

What is claimed is:

1. A physiological signal detecting apparatus, comprising:
a physiological signal detecting device including:
    a carrier having a first surface and a second surface opposite the first surface;
    two electrode layers comprising a first electrode layer and a second electrode layer, wherein the two electrode layers are separately fixed on the first surface of the carrier; and
    two signal transmitters comprising a first signal transmitter and a second signal transmitter, wherein the first signal transmitter buckles the first electrode layer, onto the carrier, and the second signal transmitter buckles the second electrode layer, wherein the first signal transmitter contacts and corresponds in position to the first electrode layer, the second signal transmitter contacts and corresponds in position to the second electrode layer, and each of the two signal transmitters consists of:
        a transmitting member integrally formed as one-piece structure and including a first sheet, a column perpendicularly extending from the first sheet, and a plurality of thorns curvedly extending from the first sheet; and
        an external connector integrally formed as one-piece structure and including a ring-shaped second sheet and a hollow protrusion extending from an inner edge of the second sheet,
    wherein in the first signal transmitter and the first electrode layer, the first sheet abuts against the first electrode layer, each of the thorns has a piercing end having an acute angle piercing into the first electrode layer, the column passes through the first electrode layer and the carrier, a free end portion of the column is exposed from the carrier, and the protrusion is sleeved at and fastened to the free end portion of the column so that the carrier and the first electrode layer are sandwiched between the second sheet and the first sheet,
    wherein in the second signal transmitter and the second electrode layer, the first sheet abuts against the second electrode layer, each of the thorns has a piercing end piercing into the second electrode layer, the column passes through the second electrode layer and the carrier, a free end portion of the column is exposed from the carrier, and the protrusion is sleeved at and fastened to the free end portion of the column so that the carrier and the second electrode layer are sandwiched between the second sheet and the first sheet; and
a signal transceiver including two electrical contacts respectively and detachably positioned at the protrusions of the two signal transmitters, wherein each of the two electrode layers is configured for receiving a physiological signal, the first signal transmitter is configured for transmitting the physiological signal from the first electrode layer to the signal transceiver through the thorns thereof, and the second signal transmitter is configured for transmitting the physiological signal from the second electrode layer to the signal transceiver through the thorns thereof.

2. The physiological signal detecting apparatus as claimed in claim 1, wherein each of the thorns includes an outer surface having an arced shape and defining a tangential direction parallel to the piercing end thereof, the tangential direction defined by each of the thorns of the first signal transmitter is substantially perpendicular to the first electrode layer, and the tangential direction defined by each of the thorns of the second signal transmitter is substantially perpendicular to the second electrode layer.

3. The physiological signal detecting apparatus as claimed in claim 2, wherein in each of the two signal transmitters, the first sheet has a plurality of notches in a ring-shaped arrangement, and each of the notches has an acute angle aligning a center of the first sheet, the thorns respectively correspond in shape to the notches, the volume of each of the thorns is equal to that of the corresponding notch, and each of the thorns curvedly extends from an inner wall of the corresponding notch.

4. A physiological signal detecting device, comprising:
a carrier having a first surface and a second surface opposite the first surface;
an electrode layer fixed on the first surface of the carrier; and
a signal transmitter buckled on the electrode layer and the carrier and including:
    a transmitting member integrally formed as one-piece structure and including a first sheet, a column perpendicularly extending from the first sheet, and a thorn curvedly extending from the first sheet, wherein the first sheet abuts against the electrode layer, the thorn has a piercing end having an acute angle piercing into the electrode layer, the column passes through the electrode layer and the carrier, and a free end portion of the column exposes from the carrier; and
    an external connector integrally formed as one-piece structure and including a ring-shaped second sheet and a hollow protrusion extending from an inner edge of the second sheet, wherein the protrusion is sleeved at and fastened to the free end portion of the column so that the carrier and the electrode layer are sandwiched between the second sheet and the first sheet; wherein the electrode layer is configured for receiving a physiological signal, and the signal transmitter is configured for transmitting the physiological signal from the electrode layer through the thorn.

5. The physiological signal detecting device as claimed in claim 4, wherein the thorn includes an outer surface having an arced shape and defining a tangential direction parallel to the piercing end, and the tangential direction defined by the thorn is substantially perpendicular to the electrode layer.

6. The physiological signal detecting device as claimed in claim 5, wherein the first sheet has a notch corresponding in shape to the thorn, the volume of the thorn is equal to that of the notch, and the thorn curvedly extends from an inner wall of the notch.

7. The physiological signal detecting device as claimed in claim 4, wherein the electrode layer includes a fixing surface and a contacting surface opposite the fixing surface, the fixing surface is disposed on the first surface of the carrier, and the contacting surface abuts against the first sheet, the piercing end of the thorn pierces into the electrode layer through the contacting surface, the thorn is entirely embedded in the electrode layer, and at least part of the contacting surface is configured for touching a person to receive a physiological signal from the person.

8. The physiological signal detecting device as claimed in claim 4, wherein the free end portion of the column has a buckling trough, the protrusion includes a head portion and a neck portion connected to the head portion and the inner edge of the second sheet, and the neck portion detachably buckles the buckling trough.

9. The physiological signal detecting device as claimed in claim 8, wherein the neck portion includes a plurality of ribs formed by punching an outer surface thereof, the ribs are in a ring-shaped arrangement, and at least two of the ribs detachably buckle the buckling trough.

10. The physiological signal detecting device as claimed in claim 4, wherein a projecting region defined by orthogonally projecting the first sheet in a longitudinal direction of the column onto the second sheet has an outer edge substantially overlapped at an outer edge of the second sheet.

* * * * *